United States Patent [19]

Lillwitz

[11] 4,448,987

[45] May 15, 1984

[54] CATALYZED HYDROGENATION OF TEREPHTHALIC ACID TO P-HYDROXYMETHYLBENZOIC ACID USING A RHENIUM CATALYST

[75] Inventor: Lawrence D. Lillwitz, Glen Ellyn, Ill.

[73] Assignee: Standard Oil Company (Indiana), Chicago, Ill.

[21] Appl. No.: 445,547

[22] Filed: Nov. 30, 1982

[51] Int. Cl.$^3$ ............................................... C07C 65/04
[52] U.S. Cl. .................................... 562/473; 560/64; 568/811; 568/814
[58] Field of Search .......................... 562/473; 560/64; 568/811, 814

[56] References Cited

FOREIGN PATENT DOCUMENTS 50-35064 11/1980 Japan ................................. 568/814

OTHER PUBLICATIONS

Broadbent, H. S. et al., JACS, 81 3587–3589, (1959).

Primary Examiner—Paul J. Killos
Attorney, Agent, or Firm—William C. Clarke; William T. McClain; William H. Magidson

[57] ABSTRACT

A process is disclosed for preparation of hydroxymethyl aryl monocarboxylic acid compounds by reduction of arylene dicarboxylic acid compounds in the presence of a rhenium catalyst and an aqueous solvent.

13 Claims, No Drawings

CATALYZED HYDROGENATION OF TEREPHTHALIC ACID TO P-HYDROXYMETHYLBENZOIC ACID USING A RHENIUM CATALYST

FIELD OF THE INVENTION

This invention relates to a method of making hydroxymethyl aryl monocarboxylic acid compounds from arylene dicarboxylic acids in a catalyzed hydrogenation. More particularly, it relates to the selective reduction of terephthalic and isophthalic acids with a rhenium catalyst to hydrogenate one carboxylic acid group to a hydroxymethyl group and yet is selective enough to prevent hydrogenolysis of the hydroxymethyl group to the methyl derivative and reduction of the second carboxylic acid group to the hydroxymethyl group or to the methyl derivative.

BACKGROUND OF THE INVENTION

Hydroxymethyl aryl monocarboxylic acids such as p-hydroxymethylbenzoic acid, m-hydroxymethylbenzoic acid, and 6-hydroxymethyl-2-naphthoic acid are known in the art. Of particular interest has been p-hydroxymethylbenzoic acid (p-HMBA), which has been synthesized for use as a monomer to make the corresponding homopolymer, poly(p-methylenebenzoate) and its corresponding ester, methyl p-hydroxymethylbenzoate (mep-HMB). The acid is believed to have been prepared first as early as 1872 by free-radical bromination of p-toluic acid to p-bromomethyltoluic acid, hydrolysis with aqueous barium hydroxide, and subsequent purification by recrystallization from water.

A process has now been found for the hydrogenation of arylene dicarboxylic acids wherein one carboxylic acid group is hydrogenated to a hydroxymethyl group using a rhenium catalyst and yet is selective enough to prevent hydrogenolysis of the hydroxymethyl group to the methyl group and reduction of the second carboxylic acid to a hydroxymethyl group or to a methyl group. More specifically, a process has been found for the preparation of p-hydroxymethylbenzoic acid by the reduction of terephthalic acid in the presence of a rhenium catalyst under relatively mild conditions wherein conversion of terephthalic acid is within the range of from about 20 to 30(wt)% and selectivity to p-hydroxymethylbenzoic acid is within the range of from about 80 to 90%. Yields are accordingly within the range of from about 18 to about 27(wt)% of terephthalic acid feed. The invented process can be used also to prepare m-hydroxymethylbenzoic acid and 6-hydroxymethyl-2-naphthoic acid.

Rhenium oxide catalysts have been known as excellent catalysts for the liquid-phase reduction of a variety of organic substrates. Broadbent, et al., *J. Organic Chem.*, 28, 2345 (1963) teaches rhenium VI oxide is a very efficient catalyst for the hydrogenation of carboxylic acids and carboxamides. Broadbent reported that benzoic acid, ethylbenzoate, benzaldehyde, and m-nitrobenzaldehyde were reduced to the corresponding aromatic carbinols instead of suffering hydrogenolysis to the toluenes which result from most catalytic hydrogenations. Broadbent, et al., ibid., 24, 1847 (1959) teaches that the catalytic substrate reduction activity of rhenium catalysts on aliphatic compounds differs for rhenium catalysts, also concurrently reduced, using different solvents. Broadbent teaches, op. cit., that rhenium heptoxide is reduced in situ as catalyst and reduces maleic acid with no solvent to 91% succinic acid and 9% 1,4-butanediol; that succinic acid with no solvent is reduced to 94% 1,4-butanediol and 6% n-butyl alcohol; but that succinic acid in p-dioxane is reduced to 61% butyrolactone, 33% 1,4-butanediol and 6% polyesters. Trivedi, et al., *JAOCS*, 17, January 1981, teaches that addition of ruthenium on carbon (Ru/C) to a rhenium heptoxide ($Re_2O_7$) catalyst gave a synergistic effect in reduction of an aliphatic monocarboxylic acid to a primary alcohol at a temperature of 170° C. and 2500 psi in a 1,4 dioxane solvent but at higher temperatures and lower pressures (230° C. and 500 psi) hydrocarbons were the major or exclusive products. J. E. Carnahan, et al., *JACS*, 77, 3766, July 20, 1955, teaches that in rutheniumcatalyzed hydrogenation of adipic acid in water, hexamethylene glycol resulted at temperatures of 150° to 175° C. and pressures of 520–700 atmospheres. However, none of the above publications teach, disclose or suggest that a rhenium catalyst can be used to hydrogenate arylene dicarboxylic acids to hydroxymethyl aryl monocarboxylic acids wherein one carboxylic acid group is hydrogenated to a hydroxymethyl group and the other acid group is not reduced.

Unexpectedly it has been found that a rhenium oxide catalyst has catalytic activity in aqueous solvent to selectively reduce arylene dicarboxylic acids to the hydroxymethyl aryl monocarboxylic acids. Only one acid group of the arylene dicarboxylic acid is reduced to a hydroxymethyl moiety.

Accordingly, it is an object of this invention to prepare hydroxymethyl aryl monocarboxylic acids from arylene dicarboxylic acids by hydrogenation using a rhenium catalyst.

It is a further object of this invention to prepare p- and m-hydroxymethylbenzoic acids by reduction of terephthalic acid and isophthalic acid in the presence of a rhenium catalyst and an aqueous solvent.

It is a further object of this invention to provide a process for the preparation of p- and m-hydroxymethylbenzoic acids wherein terephthalic acid and isophthalic acid are directly reduced to p- and m-hydroxymethylbenzoic acids instead of to p- or m-xylene or dihydroxymethylbenzenes. Other objects will appear hereinafter.

SUMMARY OF THE INVENTION

A process is disclosed for preparation of p- and m-hydroxymethylbenzoic acids by reduction of terephthalic and isophthalic acids in the presence of a rhenium catalyst and an aqueous solvent at a temperature of from about 140° to about 200° C.

DETAILS OF THE INVENTION

The process of the instant invention relates to the preparation of p- and m-hydroxymethylbenzoic acids by reduction of terephthalic acid and isophthalic acid in the presence of a rhenium oxide catalyst and an aqueous solvent. Since rhenium oxides are known to be reduced in hydrogen at temperatures above 140° C., it is considered that the rhenium oxide catalyst is reduced in situ to the lower oxides and rhenium metal with reduction of the substrate. Rhenium trioxide can be the rhenium oxide utilized as catalyst but rhenium heptoxide and rhenium tetraoxide can also be used as catalysts. The ratio of rhenium oxide catalyst to arylene dicarboxylic acid is within the range of from about 1% to about 25% upon a weight basis since the amount of rhenium oxide present is not critical. A convenient ratio is from 1% to 10% of the weight of the reactant acid with preference to lower amounts because of the cost of the catalyst. The presence of metal catalysts other than rhenium oxides is deleterious to the reduction of arylene dicarboxylic acids to hydroxymethyl aryl monocarboxylic acids. For example, use of a rhenium trioxide/ruthenium on carbon catalyst in aqueous solution preferentially reduced terephthalic acid to ring hydrogenated products and not to p-hydroxymethylbenzoic acid.

The selective reduction of arylene dicarboxylic acids to hydroxymethyl aryl monocarboxylic acids is temperature-dependent. It is an essential element of the invented process that the temperature of the reaction be held within the range of from about 140° C. to about 200° C. In the presence of aqueous solvent and a rhenium catalyst, terephthalic acid is preferentially reduced to xylene and toluic acid at a temperature greater than about 200° C. Below 140° C., the reaction proceeds so slowly as to not have economic value.

The pressure at which the process is operated is not critical. It has been found to be convenient to conduct the process at a pressure within the range of from about 1400 psig to about 2200 psig to facilitate the rate of reaction. A higher pressure can be used if desired, up to about 3000 psig, and various methods of introducing the hydrogen into the reaction mixture can be used. For example, hydrogen under pressure can be conveniently passed through the reaction mixture to stir the mixture and aid in the speed of the reaction.

The ratio of hydrogen to reactant is determined by hydrogen pressure and temperature of the reaction mixture. Excess hydrogen is made available since the reaction of hydrogen with the reactant is limited by the solubility of hydrogen in water. It is convenient accordingly to utilize hydrogen at a temperature and pressure wherein rate of reaction with the reactant is maximized as can be determined by experiment.

Reaction rate of the invented process is also determined by the solubility of the reactant in water. Since terephthalic acid and isophthalic acid are sparing soluble in water, use of watersoluble salts of these acids improves the reaction rate. Suitable salts are those alkali metal compounds of Group IA metals of the Periodic Table of Elements, as contained on the inside cover of *Handbook of Chemistry and Physics,* 46th Edition, published by The Chemical Rubber Company, including sodium, potassium, lithium, cesium and rubidium. Ammonium compounds such as the hydroxide can also be used. The reactant acid can react with up to two mole equivalents of the Group IA metal per mole of dicarboxylic acid, but one mole of Group IA metal per mole of dicarboxylic acid is useful. Conversion of only one acid group to the ammonium or alkali metal salt will increase solubility without blocking the other acid group to hydrogenation. Preferred mole equivalents of ammonium or alkali metal ion to dicarboxylic acid is from 0 to 1 mole equivalent of ammonium or alkali metal ion to ½ mole equivalent of dicarboxylic acid.

An aqueous solution of the arylene dicarboxylic acid is an essential element of the invented process. The presence of compounds other than compounds which increase solubility of arylene dicarboxylic acids in water, such as ammonium hydroxide and basic solutions of metals of Group IA, is deleterious to the reaction. For example, in the presence of methanol, terephthalic acid is preferentially reduced to p-xylene and toluic acid and not to p-hydroxybenzoic acid.

The invention will be illustrated by the following specific examples. It should be understood, however, that the detailed expositions of the process of the invention, while indicating preferred embodiments, are given by way of illustration only since various changes and modifications within the spirit and scope of the invention will become apparent to those skilled in the art and are not intended to limit the scope of the invention.

EXAMPLE I

The apparatus used was a one-gallon stainless steel stirred autoclave (Autoclave Engineers MagneDrive) equipped with a double baffle, cooling coils for controlling internal temperature, a thermocouple for recording temperature, a 0–3000 psi pressure gauge and a 2200 psi safety release.

The catalyst in the form of rhenium trioxide, $ReO_3$ (5.0 g), was introduced into the reactor with polymer grade purified terephthalic acid (50.0 g). Water, 1500 ml, was added. The autoclave was flushed with excess nitrogen, flushed with excess hydrogen, and then pressurized with hydrogen to 1400 psi and the temperature was raised to 160° C. over a period of 45 min., and held at a temperature of 160° C. to 175° C. (1800 psi) for a period of 7 hrs. At the end of the reaction period, the autoclave was vented of hydrogen, the autoclave contents were decanted and filtered (80° C.). The filtrate analyzed 85% p-hydroxymethylbenzoic acid (p-HMBA), 6% 1,4 p-hydroxymethylbenzene (1,4 p-HMB), and 7% toluic acid. Only traces of terephthalic acid were soluble in the water filtrate. Approximately 20% of the terephthalic acid was converted to p-hydroxymethylbenzoic acid with a selectivity of 85%.

EXAMPLE II

In the procedure of Example I, 100 g of polymer grade purified terephthalic acid was reduced in the presence of $ReO_3$ (5.0 g) catalyst in water (1900 ml) containing 1.0 equivalents of $NH_4OH$ to improve the solubility of the terephthalic acid and increase conversion of terephthalic acid. After filtration of the reaction product the filtrate was neutralized with dilute HCl to precipitate the free carboxylic acid. Process details and results are given in Table I.

TABLE I

| Temperature | 180–200° C. | 22% conversion | | |
|---|---|---|---|---|
| Pressure | 1700–1800 psi | Selectivities | | |
| | | | | toluic |
| Time | 9¼ hrs. | p-HMBA | 1,4 p-HMB | acid |
| | | 55% | 14% | 23% |

EXAMPLE III

The apparatus used was an Autoclave Engineers MagneDrive one-liter stainless steel stirred autoclave equipped with cooling coils for controlling internal temperature, a thermocouple for recording temperature, 0–3000 psi pressure gauge and a 2000 psi safety release. Following the procedure in Example I, 20.0 g of polymer grade purified terephthalic acid were reduced in the presence of $Re_2O_7/5\%$ ruthenium on carbon (1:1) catalyst (2.0 g) in water (400 ml). Process details and results are given in Table II.

TABLE II

| Temperature | 175° C. | 90% Conversion |
|---|---|---|
| Pressure | 1600 psi | Selectivities |

TABLE II-continued

| Time | 7 hrs. | 70% 1,4 cyclohexane decarboxylic acid |
| --- | --- | --- |
| | | 30% unknown ring hydrogenation products |

EXAMPLE IV

Example III was repeated exactly except that the reaction was run for only 2 hours. Only 50% of the terephthalic acid was converted with 90% selectivity to 1,4 cyclohexane dicarboxylic acid and no p-HMBA.

The above data in Examples III and IV teach that the mixed $Re_2O_7/Ru/C$ catalyst in water solution preferentially reduces terephthalic acid to ring hydrogenated products and not p-HMBA.

EXAMPLE V

In the procedure of Example I, 5.0 g of terephthalic acid were reduced in the presence of a rhenium trioxide catalyst in a water/methanol solution. Process details and results are in Table III.

TABLE III

Reduction of Terephthalic Acid
Rhenium Oxide Catalyst/Water/Methanol

| Conditions | |
| --- | --- |
| Terephthalic Acid, g | 5.0 |
| $ReO_3$, g | 0.5 |
| Water, (Deionized) g | 100.0 |
| Methyl Alcohol g | 0.1 |
| Temp. °C. | 200 |
| Pressure, psig | 1900 |
| Period of Reaction, Hrs. | 4 |
| Product (wt) % | |
| Terephthalic Acid | 60 |
| p-HMBA | 4.5 |
| p-Toluic Acid | 3.0 |
| p-Xylene | 25 |

The above data indicate that in a water/methanol solution terephthalic acid is reduced preferentially to p-xylene and toluic acid and not to p-hydroxymethylbenzoic acid.

EXAMPLE VI

In the procedure of Example I, 5.0 g of terephthalic acid were reduced in the presence of a rhenium trioxide catalyst in deionized water. Process details and results are in Table IV.

TABLE IV

Reduction of Terephthalic Acid
Rhenium Oxide Catalyst/Water

| Conditions | |
| --- | --- |
| Terephthalic Acid, g | 5.0 |
| $ReO_3$, g | 0.5 |
| Water (Deionized), ml | 100 |
| Temp. ° C. | 260 |
| Pressure, psig | 1900 |
| Period of Reaction, Hrs. | 4 |
| Product (wt) % | |
| Terephthalic Acid | 36 |
| p-HMBA | 12 |
| p-Toluic Acid | 24 |
| p-Xylene | 29 |

The above data indicate that in the presence of a rhenium oxide catalyst and in water solution terephthalic acid is preferentially reduced at a temperature of 260° C., to p-toluic acid and p-xylene and not to p-hydroxymethylbenzoic acid.

EXAMPLE VII

In the procedure of Example I, 50 g of polymer grade purified terephthalic acid were reduced in the presence of $ReO_3$ (5.0 g) catalyst in water (1500 ml) containing 1.0 equivalents of NaOH to improve solubility of the terephthalic acid. After filtration of the reaction product solution the filtrate was neutralized with dilute HCl to precipitate unreacted terephthalic acid. Process details and results are given in Table V.

TABLE V

| Temperature | 225° C. | 82% conversion Selectivities | | |
| --- | --- | --- | --- | --- |
| Pressure | 2000 psi | | | |
| Time | 7 hrs. | p-HMBA | 1,4 p-HMB | toluic acid |
| | | 4% | 57% | 39% |

The above data in Examples VI and VII indicate that in the presence of water, but under a condition of a temperature greater than 200° C., terephthalic acid is preferentially reduced to products other than p-hydroxymethylbenzoic acid, i.e., p-xylene, 1,4 p-hydroxymethylbenzene and p-toluic acid.

What is claimed is:

1. A process for preparing a hydroxymethyl aryl monocarboxylic acid from an arylene dicarboxylic acid which comprises hydrogenating an aqueous solution of an arylene dicarboxylic acid compound in the presence of a rhenium oxide catalyst at a temperature within the range of from about 140° C. to about 200° C.

2. The process of claim 1 wherein said aqueous solvent is substantially free of compounds other than those compounds which increase solubility of said arylene dicarboxylic acid compound in aqueous solvent.

3. The process of claim 1 wherein said aqueous solvent is substantially free of methanol.

4. The process of claim 1 wherein said aqueous solvent consists essentially of water.

5. The process of claim 1 wherein said arylene dicarboxylic acid compound is a monosalt of a member selected from the group consisting of ammonium and alkali metal compounds.

6. The process of claim 1 wherein said arylene dicarboxylic acid compound is a monoammonium salt.

7. The process of claim 1 wherein said arylene dicarboxylic acid compound is the monosodium salt.

8. The process of claim 1 wherein said rhenium oxide catalyst is rhenium trioxide.

9. The process of claim 1 wherein said rhenium catalyst is rhenium heptaoxide.

10. The process of claim 1 wherein said rhenium catalyst is rhenium tetraoxide.

11. The process of claim 1 wherein said arylene dicarboxylic acid compound is terephthalic acid.

12. The process of claim 1 wherein said arylene dicarboxylic acid compound is isophthalic acid.

13. The process of claim 1 wherein said arylene dicarboxylic acid compound is terephthalic acid, said rhenium oxide catalyst is rhenium trioxide, said aqueous solvent is water and product of said process comprises p-hydroxymethylbenzoic acid.

* * * * *